US012648747B2

(12) United States Patent
Doki

(10) Patent No.: US 12,648,747 B2
(45) Date of Patent: Jun. 9, 2026

(54) PHASE CONTRAST X-RAY IMAGING SYSTEM AND IMAGE PROCESSING METHOD

(71) Applicant: SHIMADZU CORPORATION, Kyoto (JP)

(72) Inventor: Takahiro Doki, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 170 days.

(21) Appl. No.: 18/768,669

(22) Filed: Jul. 10, 2024

(65) Prior Publication Data

US 2025/0017542 A1      Jan. 16, 2025

(30) Foreign Application Priority Data

Jul. 13, 2023     (JP) ................................. 2023-115538
Apr. 23, 2024     (JP) ................................. 2024-070056

(51) Int. Cl.
*A61B 6/00*          (2024.01)
*A61B 6/40*          (2024.01)
*A61B 6/42*          (2024.01)
*G01B 11/00*        (2006.01)
*G01N 23/00*        (2006.01)
*G01N 23/04*        (2018.01)
*G01N 23/041*       (2018.01)

(52) U.S. Cl.
CPC ............ *A61B 6/484* (2013.01); *A61B 6/4035* (2013.01); *A61B 6/4291* (2013.01); *A61B 6/5205* (2013.01); *A61B 6/5258* (2013.01);

*G01B 11/00* (2013.01); *G01N 23/00* (2013.01); *G01N 23/041* (2018.02)

(58) Field of Classification Search
CPC ..... A61B 6/4035; A61B 6/4291; A61B 6/484; A61B 6/5205; A61B 6/5258; G01B 11/00; G01N 23/00; G01N 23/041; G01N 23/046

See application file for complete search history.

(56) References Cited

U.S. PATENT DOCUMENTS 11,013,482 B2      5/2021  Morimoto et al.
2012/0183123 A1*   7/2012  Tada ................... G01N 23/046
                                              378/62

FOREIGN PATENT DOCUMENTS

JP              6743983 B2     8/2020

* cited by examiner

*Primary Examiner* — Mark R Gaworecki
(74) *Attorney, Agent, or Firm* — Maier & Maier, PLLC

(57) ABSTRACT

A phase contrast X-ray imaging system includes an X-ray source, a plurality of gratings, a detector for detecting X-rays, a grating movement mechanism, and a controller. The controller generates a phase contrast image based on intensity changes that represent changes in pixel values of pixels detected by the detector while moving a scanning grating, which is at least one of the plurality of gratings, using the grating movement mechanism. The controller acquires an analysis period representing a period of the intensity change to reduce a moire artifact, and adjusts a set value of movement of the scanning grating for generating the phase contrast image based on the analysis period acquired.

11 Claims, 4 Drawing Sheets

ANALYSIS PERIODS (Ap)

PHASE CONTRAST X-RAY IMAGING SYSTEM AND IMAGE PROCESSING METHOD

CROSS-REFERENCE TO RELATED APPLICATIONS

The related application number JP2023-115538, phase contrast X-ray imaging system and image processing method, Jul. 13, 2023, Takahiro Doki and JP2024-070056, phase contrast X-ray imaging system and image processing method, Apr. 23, 2024, Takahiro Doki upon which this patent application is based are hereby incorporated by reference.

FIELD

The present invention relates to a phase contrast X-ray imaging system and an image processing method, in particular to a phase contrast X-ray imaging system for capturing an image using a plurality of gratings.

BACKGROUND

Phase contrast X-ray imaging systems for capturing an image using a plurality of gratings are known in the art. Such a phase contrast X-ray imaging system is disclosed in Japanese Patent Publication No. JP6743983, for example.

The phase contrast X-ray imaging system disclosed in the above Japanese Patent Publication No. JP6743983 performs X-ray imaging using a Talbot-Lau interferometer, which uses the plurality of gratings, and generates a phase contrast image using a fringe scanning method. In the Talbot-Lau interferometer, images are captured a plurality of times while translating any one of the plurality of gratings in a direction perpendicular to an extension direction of a grating pattern. In the fringe scanning method, a phase contrast image is generated based on intensity changes in the pixel values of pixels of X-ray images which are captured a plurality of times while translationally moving a grating. In the fringe scanning method, on the assumption that the intensity change in the pixel value of each pixel of the X-ray images is data in phases of a function whose waveform changes in accordance with a period of the grating pattern, the waveform of the function is determined, and the phase contrast image is generated based on the function whose waveform is determined.

Here, due to a change in relative positions between the gratings caused by a thermal variation or a movement accuracy of a grating movement mechanism, the period of the intensity change in the pixel value acquired becomes different from the period of the grating pattern in some cases. In such a case, because the waveform of the function deviates from actual data, an artifact may appear as noise components in the image acquired. To address this, the phase contrast X-ray imaging system disclosed in the above Japanese Patent Publication No. JP6743983 acquires an optimal solution for the period of the function which has the period as a variable and expresses the intensity change in the pixel value on the approximation basis to prevent appearance of the artifact in the phase contrast image obtained even in a case in which a shift occurs between a period of the intensity change in the pixel value of each pixel and a period of the gratings.

Here, a shift not only occurs between the period of the intensity change in the pixel value of each pixel and the period of the gratings due to the change in relative positions between the gratings caused by the thermal variation or the movement accuracy of the grating movement mechanism, but also a shift occurs between a set value of movement of the grating and actual movement of the grating based on the set value in some cases. For example, an actual movement amount of the grating and an actual angular position of the grating may be shifted from a set value of a movement amount of the grating and a set value of an angular position of the grating. In such a case, in the fringe scanning method for generating a phase contrast image, because the period of the intensity change in the pixel value obtained becomes different from the period of the grating pattern, an artifact will appear in the phase contrast image acquired. To address this, as in the phase contrast X-ray imaging system disclosed in the above Japanese Patent Publication No. JP6743983, it can be conceived that the phase contrast image is generated by acquiring the optimal solution for the period of intensity change in the pixel value obtained and by determining the waveform of the function from the intensity change in the pixel value in each pixel of the X-ray image. However, in the phase contrast X-ray imaging system disclosed in the above Japanese Patent Publication No. JP6743983, the phase contrast image is generated by applying approximation to the intensity change in the pixel value detected under a condition in which a shift occurs between the set value of movement of the grating and actual movement of the grating based on the set value, and by determining the waveform of the function, which expresses the intensity change. For this reason, if the shift between the set value of movement of the grating and the actual movement of the grating based on the set value is large, even when the phase contrast image is generated by determining the waveform of the function from the intensity change in the pixel value in each pixel of the X-ray image as in the phase contrast X-ray imaging system disclosed in the above Japanese Patent Publication No. JP6743983, because the phase contrast image is generated based on the intensity change in the pixel value detected under the condition in which the shift occurs between the set value and the actual movement, an artifact (moire artifact) included in the phase contrast image cannot be sufficiently reduced. From this viewpoint, it is desired to reduce the moire artifact in the phase contrast image generated even if the shift between the set value of movement of the grating and the actual movement of the grating is large.

SUMMARY

The present invention is intended to solve the above problem, and one object of the present invention is to provide a phase contrast X-ray imaging systems and an image processing method capable of reducing a moire artifact in a phase contrast images generated even if a shift between a set value of movement of a grating and actual movement of the grating is large.

In order to attain the aforementioned object, a phase contrast X-ray imaging system according to a first aspect of the present invention includes an X-ray source; a plurality of gratings including a first grating for forming a self-image by irradiation with X-rays from the X-ray source, and a second grating for interfering with the self-image of the first grating; a detector for detecting the X-rays for irradiation from the X-ray source; a grating movement mechanism for moving at least one of the plurality of gratings; and a controller for generating a phase contrast image based on intensity changes that represent changes in pixel values of pixels detected by the detector while moving a scanning grating, which is the at least one of the plurality of gratings, using the grating movement mechanism, wherein the controller is configured to acquire an analysis period that represents a period of the intensity change to reduce a moire artifact as a noise component included in the phase contrast image, and to adjust a set value of movement of the scanning grating for generating the phase contrast image based on the analysis period acquired.

In order to attain the aforementioned object, an image processing method according to a second aspect of the present invention includes detecting X-rays for irradiation from an X-ray source that passes through a plurality of gratings while moving a scanning grating, which is at least one of the plurality of gratings including a first grating for forming a self-image by irradiation with X-rays from the X-ray source and a second grating for interfering with the self-image of the first grating; generating a phase contrast image based on intensity changes that represent changes in pixel values of pixels detected; acquiring an analysis period that represents a period of the intensity change to reduce a moire artifact as a noise component in the phase contrast image generated; and adjusting a set value of movement of the scanning grating for generating the phase contrast image based on the analysis period acquired.

In the phase contrast X-ray imaging system according to the first aspect, and the image processing method according to the second aspect of the present invention, as discussed above, the analysis period that represents a period of the intensity change is acquired to reduce the moire artifact, which is a noise component included in the phase contrast image. In addition, in the phase contrast X-ray imaging system according to the first aspect, and the image processing method according to the second aspect, the set value of movement of the scanning grating for generating the phase contrast image is adjusted based on the analysis period acquired. According to this configuration, because the set value of movement of the scanning grating for generating the phase contrast image is adjusted based on the analysis period acquired, the set value can be adjusted to reduce a shift of actual movement of the grating with respect to the set value of movement of grating. Accordingly, the phase contrast image can be generated based on the intensity change in the pixel value detected under a condition in which the shift with respect to the set value of movement of grating is reduced. Consequently, it is possible to reduce a moire artifact in the phase contrast image generated even if the shift between the set value of movement of the grating and the actual movement of the grating based on the set value is large.

DETAILED DESCRIPTION

Embodiments embodying the present invention will be described with reference to the drawings.

The following description describes a configuration of a phase contrast X-ray imaging system 100 according to one embodiment of the present invention with reference to FIGS. 1 to 7.

(Configuration of Phase Contrast X-Ray Imaging System)

Figures 1, 2:
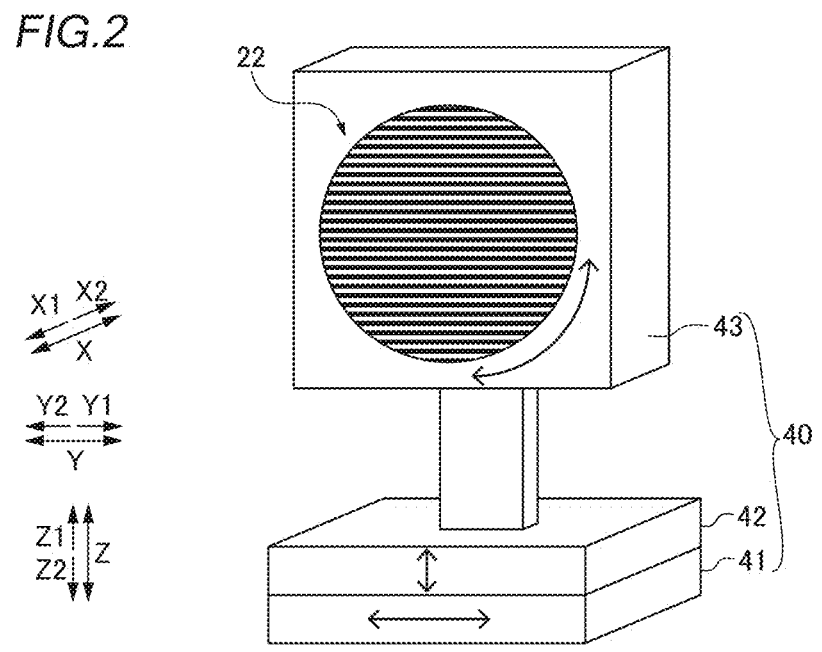
FIG. 1 is a schematic view showing a phase contrast X-ray imaging system according to one embodiment of the present invention as viewed in a Y direction.
FIG. 2 is a schematic view illustrating a configuration of a grating movement mechanism.

The following description first describes a configuration of the phase contrast X-ray imaging system 100 according to the one embodiment of the present invention with reference to FIG. 1. The phase contrast X-ray imaging system 100 is a system for providing an internal image of a subject 101 by using phase difference between X-rays passing through the subject 101. Also, the phase contrast X-ray imaging system 100 is a system for providing an internal image of the subject 101 based on a fringe scanning method by using a Talbot-Lau interferometer. For example, the phase contrast X-ray imaging system 100 is used to provide an internal image of the subject 101 as an object in a non-destructive inspection application.

FIG. 1 is a view showing the phase contrast X-ray imaging system 100 as viewed in a Y direction. As shown in FIG. 1, the phase contrast X-ray imaging system 100 includes an X-ray source 11, a detector 12, a plurality of gratings 20, a controller 30 and a grating movement mechanism 40. The plurality of gratings 20 include a first grating 21, a second grating 22, and a third grating 23. In this specification, a direction from the X-ray source 11 toward the first grating 21 is defined as an X2 direction, while a direction opposite to the X2 direction is defined as an X1 direction. The X direction is a direction of an irradiation axis of X-rays from the X-ray source 11, which is a direction from the X-ray source 11 toward the detector 12. Also, a leftward/rightward direction in a plane perpendicular to the X direction is defined as the Y direction, directions pointing into and out of the paper are defined as Y2 and Y1 directions, respectively. In addition, an upward/downward direction in the plane perpendicular to the X direction is defined as a Z direction, and upward and downward directions are defined as Z1 and Z2 directions, respectively. In the phase contrast X-ray imaging system 100, the X-ray source 11, the third grating 23, the first grating 21, the second grating 22, and the detector 12 are arranged in this order along the irradiation axis of X-rays (X direction). That is, the first grating 21, the second grating 22, and the third grating 23 are interposed between the X-ray source 11 and the detector 12. The second grating 22 is an example of a "scanning grating" in the claims. Also, the Y direction and the Z direction are an example of a "first direction" and an example of a "second direction", respectively, in the claims.

The X-ray source 11 irradiates the subject 101 with X-rays. The X-ray source 11 includes an X-ray tube configured to generate X-rays when a high voltage is applied from a power supply (not shown) based on signals from the controller 30. The X-ray source 11 is configured to direct the X-rays generated to the detector 12 (in the X2 direction).

The detector 12 detects X-rays with which the subject is irradiated by the X-ray source 11. The detector 12 is configured to convert the X-rays detected into electrical signals and to read the electrical signals converted as image signals. The detector 12 is a flat panel detector (FPD), for example.

The detector 12 includes a plurality of converters (not shown), and a plurality of pixel electrodes (not shown) arranged on the plurality of converters. The plurality of converters and the plurality of pixel electrodes are arranged at a predetermined periods (pixel pitches) in the Y and Z directions in an array in a YZ plane. Also, the detector 12 is configured to output the image signal obtained to the controller 30. The YZ plane is an example of a "perpendicular plane" in the claims.

The first grating 21 has a plurality of slits 21a and X-ray phase change parts 21b, which are arranged at a predetermined period (pitch) $p_1$ in a predetermined direction in the YZ plane. The period (pitch) $p_1$ is the sum of sizes of one slit 21a and one X-ray phase change part 21b in a width direction of a grating pattern. The slits 21a and the X-ray phase change parts 21b are formed to linearly extend. Also, the slits 21a and the X-ray phase change parts 21b are formed to extend parallel to each other. The first grating 21 is arranged between the X-ray source 11 and the second grating 22, and is irradiated with X-rays from the X-ray source 11. When coherent X-rays pass through a grating having the slits, an image of the grating (self-image 50) is formed at a certain distance (Talbo distance) from the grating. This is called the Talbo effect. The first grating 21 is a phase grating used to form the self-image 50 of the first grating 21 (see FIG. 3) by using the Talbot effect.

The second grating 22 has a plurality of X-ray transmission parts 22a and X-ray absorption parts 22b, which are arranged in a predetermined period (pitch) $p_2$ in a predetermined direction in the YZ plane. The period (pitch) $p_2$ is the sum of sizes of one X-ray transmission part 22a and one X-ray absorption part 22b in a width direction of a grating pattern. The X-ray transmission parts 22a and the X-ray absorption parts 22b are formed to linearly extend. Also, the X-ray transmission parts 22a and the X-ray absorption parts 22b are formed to extend parallel to each other. The second grating 22 is an absorption grating for interfering with the self-image 50 of the first grating 21. Although the first grating 21 and the second grating 22 have different functions, functions of the slits 21a of the first grating and the X-ray transmission parts 22a of the second grating are to transmit X-rays. Also, the X-ray absorption parts 22b serve to cut off X-rays, and the X-ray phase change parts 21b change a phase of X-rays because the X-ray phase change parts have a different refractive index from the slits 21a. The second grating 22 is arranged between the first grating 21 and the detector 12 so that the second grating is irradiated with X-rays that pass through the first grating 21. Also, the second grating 22 is arranged at a position spaced at the Talbo distance away from the first grating 21. The second grating 22 interferes with the self-image 50 of the first grating 21 so that a moire fringe (not shown) is formed on a detection plane of the detector 12.

The third grating 23 has a plurality of slits 23a and X-ray absorption parts 23b, which are arranged at a predetermined period (pitch) $p_3$ in a predetermined direction in the YZ plane. The period (pitch) $p_3$ is the sum of sizes of one slit 23a and one X-ray absorption part 23b in a width direction of a grating pattern. The slits 23a and the X-ray absorption parts 23b are formed to linearly extend. Also, the slits 23a and the X-ray absorption parts 23b are formed to extend parallel to each other. The third grating 23 is arranged between the X-ray source 11 and the first grating 21, and is irradiated with X-rays from the X-ray source 11. The third grating 23 is configured to change X-rays into stripes of X-rays corresponding to positions of the slits 23a as a stripe-pattern light source after the X-rays pass through the slits 23a. As a result, the third grating 23 improves coherence of X-rays for irradiation from the X-ray source 11. That is, the third grating 23 is a multi-slit for improving coherence of X-rays from the X-ray source 11.

The grating movement mechanism 40 moves at least one of the plurality of gratings 20 based on a signal from the controller 30. For example, the grating movement mechanism 40 is configured to move the second grating 22 in a series of steps in a scanning direction, which is the width direction of the grating pattern of the second grating 22 in a grating plane (YZ plane), which is a plane perpendicular to the irradiation axis of X-rays. The scanning direction is a direction perpendicular to an extension direction of the grating pattern in the grating plane, and is a direction in which the X-ray transmission parts 22a and the X-ray absorption parts 22b of the second grating 22 are aligned (a direction of the period $p_2$). The grating movement mechanism 40 moves the second grating 22 in a series of steps of $p_2/N$ in the scanning direction so that each step is obtained by dividing the period $p_2$ of the second grating 22 by N. Here, N is a positive integer, and can be N=4, for example.

As shown in FIG. 2, the grating movement mechanism 40 includes a first movement mechanism 41, a second movement mechanism 42, and a rotation mechanism 43. The first movement mechanism 41 moves the second grating 22 in the Y direction. The second movement mechanism 42 moves the second grating 22 in the Z direction perpendicular to the Y direction. The rotation mechanism 43 rotates the second grating 22 in the YZ plane. That is, the rotation mechanism 43 rotates the second grating 22 to vary an angular position of the second grating 22 so as to vary the extension direction of the grating pattern of the second grating 22 in the YZ plane perpendicular to the irradiation axis of X-rays. That is, the rotation mechanism 43 changes the scanning direction of the second grating 22 by varying the angular position of the second grating 22 in the YZ plane. The first movement mechanism 41 and the second movement mechanism 42 linearly move the second grating 22 in the Y and Z directions, respectively, independently of the angular position of the second grating 22 in the YZ plane.

In this embodiment, the grating movement mechanism 40 is configured to move the second grating 22 for one period $p_2$ of the second grating 22 in the scanning direction by moving the second grating 22 by a scanning amount of the movement that is set in a predetermined movement direction, which is one of the Y and Z directions, independently of the angular position of the second grating 22 in the YZ plane. For example, if the second grating 22 is orientated at an angular position of 45 degrees inclined with respect the Y direction, the second grating is moved in a series of steps of $\sqrt{2}$ times $p_2/N$ in the Y direction by using the first movement mechanism 41 so that the second grating 22 is moved in a series of steps of $p_2/N$ in the scanning direction that corresponds to the angular position. For example, the first movement mechanism 41, the second movement mechanism 42, and the rotation mechanism 43 include stepping motors, piezo actuators, and the like.

The grating movement mechanism 40 is configured to vary angular positions of the first grating 21 and the third grating 23 to agree with the angular position of the second grating 22 when varying the angular position of the second grating 22 by using the rotation mechanism 43. The plurality of gratings 20 (first grating 21, second grating 22, and third grating 23) have grating patterns aligned in the common YZ plane. Even when the angular position of the second grating 22 is varied by the rotation mechanism 43, the plurality of gratings 20 are orientated to direct extension directions of their grating patterns to a common direction.

As shown in FIG. 1, the controller 30 includes a device controller 31, and an image processor 32. The controller 30 controls operations of parts of the phase contrast X-ray imaging system 100. The controller 30 includes a computing device (processor), such as a CPU (Central Processing Unit), a GPU (Graphics Processing Unit) or an FPGA (Field-Programmable Gate Array) configured for image processing, a memory, such as a ROM (Read Only Memory) and a RAM (Random Access Memory), and a storage including a non-volatile memory, such as HDD (hard disk drive) or SSD (solid state drive). The controller 30 controls the operations of the parts of the phase contrast X-ray imaging system 100 based on parameters stored in the storage and various programs.

The device controller 31 is configured to control operations of the X-ray source 11 and the grating movement mechanism 40. The device controller 31 moves the second grating 22 by controlling the operation of the grating movement mechanism 40 so that the second grating 22 moves in a series of steps in the scanning direction, for example. The device controller 31 is constructed of software as a functional block realized by executing the various programs stored in the storage by the computing device of the controller 30. The device controller 31 may be constructed of hardware by providing a dedicated processor (processing circuit). The image processor 32 is configured to generate a phase contrast image 52 based on an intensity distribution of X-rays detected by the detector 12. Specifically, the image processor 32 is configured to generate X-ray images (not shown) based on image signals output from the detector 12. Also, the image processor 32 is configured to generate phase contrast images 52 (see FIG. 4) based on the X-ray images generated. The phase contrast images 52 generated are stored in the storage. The image processor 32 is constructed of software as a function block realized by executing the various programs by the computing device (processor). The image processor 32 may be constructed of hardware by providing a dedicated processor (processing circuit). A configuration of the image processor 32 that generates the phase contrast images 52 will be described in detail later. In addition, the controller 30 previously stores set angles that are set for the angular position of the second grating 22 in the YZ plane, and a scanning amount of movement that is set for a movement amount of the second grating 22 to be moved by the grating movement mechanism 40 as set values of the movement of the second grating 22.

(Generation of Phase Contrast Image)

Figure 3:
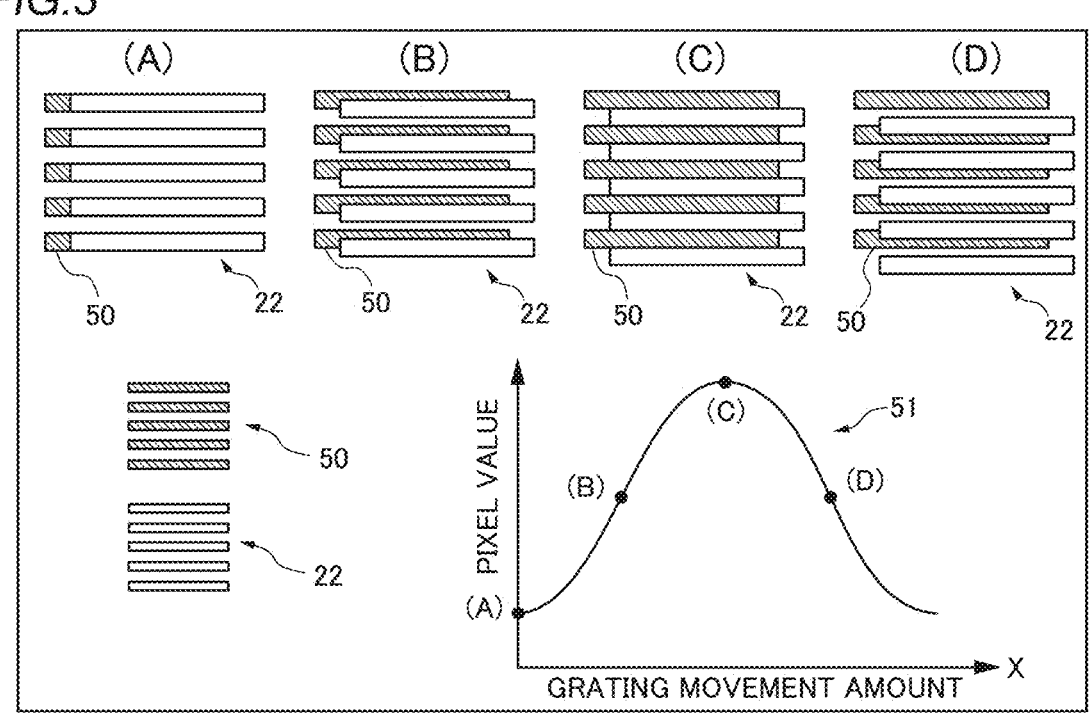
FIG. 3 is a schematic diagram illustrating processes for acquiring an intensity change of a pixel value in a pixel.

As shown in FIG. 3, the controller 30 acquires intensity changes 51 in pixel values of pixels of X-ray image data (X-ray image) detected by the detector 12. In this embodiment, the controller 30 generates the phase contrast images 52 (see FIG. 4) based on the intensity changes 51 that represent changes in the pixel values of the pixels detected by the detector 12 using a fringe scanning method while moving the second grating 22 by a predetermined scanning amount that is previously set using the grating movement mechanism 40. The controller 30 acquires each intensity change 51 by moving the second grating 22 using the grating movement mechanism 40 to move the second grating 22 for one period $p_2$ of the second grating 22 in the scanning direction based on the set angle. In FIG. 3, positional relationships between the self-image 50 of the first grating 21 and the second grating 22 are shown in schematic diagrams (A) to (D) in a case in which the second grating 22 is translationally moved in the scanning direction by the grating movement mechanism 40, and the intensity change 51 of the pixel value is shown in the X-ray images that are captured while the second grating 22 is translationally moved in a graph when a phase contrast images 52 is generated by using the fringe scanning method.

As shown in the schematic diagrams (A) to (D) in FIG. 3, the controller 30 is configured to capture images while moving the second grating 22 in a predetermined movement direction using the grating movement mechanism 40 to translationally move the second grating by $p_2/4$ in four steps in the predetermined scanning direction, which is the width direction of the grating pattern. Also, the controller 30 acquires the intensity change 51 as shown in the graph in FIG. 3 as the intensity change in the pixel value of each pixel when the images are captured taken while moving the second grating 22 by $p_2/4$ in the scanning direction for one period of the grating (for period $p_2$). In other words, the predetermined scanning amount is previously set as the movement amount of the second grating 22 to be moved by the grating movement mechanism 40 so as to move the second grating 22 the same distance in the scanning direction as the period $p_2$.

In the fringe scanning method, the phase contrast image 52 is generated based on intensity changes 51 in an X-ray image that is captured without the subject 101 and intensity changes 51 in an X-ray image that is captured with the subject 101.

Figure 4:
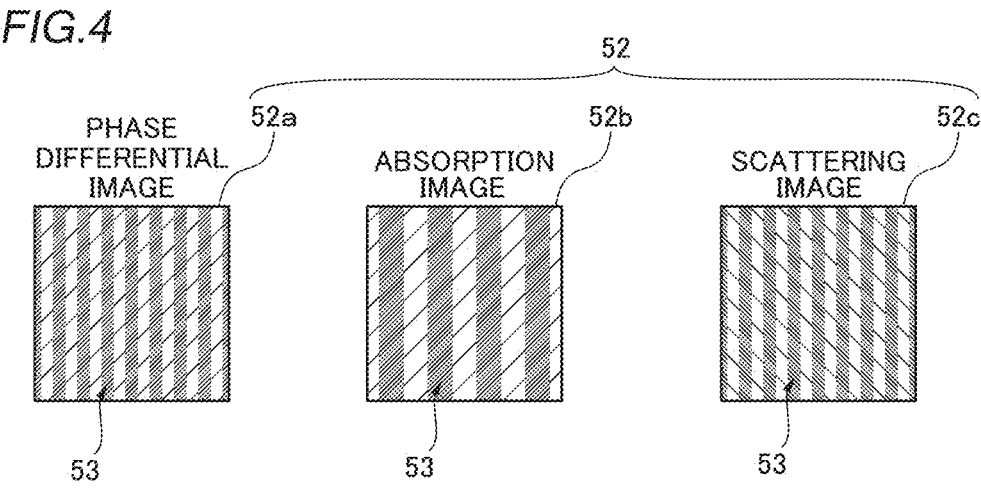
FIG. 4 is a diagram illustrating a shift of a period of the intensity change in a pixel value in each pixel.

As shown in FIG. 4, the phase contrast images 52 include a phase differential image 52*a*, an absorption image 52*b*, and a scattering image 52*c*, for example. The phase differential image 52*a* is imaged based on shifts of phases of X-rays that occur when the X-rays pass through the subject 101. The absorption image 52*b* is imaged based on attenuations of X-rays that occur when the X-rays pass through the subject 101. The scattering image 52*c* (small-angle scattering image) is a Visibility image obtained based on changes of Visibility based on small-angle scattering of an object. The scattering image 52*c* is also called a dark-field image. The "Visibility" refers to interferometric visibility.

For example, the controller 30 generates a phase contrast image 52 by fitting a shape of a waveform (see FIG. 3) of each intensity change 51 acquired when the second grating 22 is translated N times to a trigonometric function having a period p. For example, the fitting function is set as the following Equation (1).

[Formula 1]

$$y = a\sin\frac{2\pi}{p}x + b\cos\frac{2\pi}{p}x + c \tag{1}$$

where p is a value that is set as a period of the intensity change 51, and a, b, and c are coefficients of the function that are determined by determining the period p.

The controller 30 generates the phase contrast image 52 by determining the coefficients a to c in the function of Equation (1) at N data points on each intensity change 51 acquired by fitting using the least-squares method. To calculate each pixel value of the phase contrast image 52, the following Equation (2) to which the above Equation (1) is rewritten is used.

[Formula 2]

$$y = A\sin\left(\frac{2\pi}{p}x + B\right) + C \tag{2}$$

Coefficients A, B and C and the coefficients a, b and c have relationships represented by the following Equations (3) to (5). In the Equation (4), rad is used as a unit.

[Formula 3]

$$A = \sqrt{a^2 + b^2} \tag{3}$$

$$B = \tan^{-1}\left(\frac{b}{a}\right) \tag{4}$$

$$C = c \tag{5}$$

Using the coefficients A, B and C in the above Equation (2), values of each pixel in the phase differential image 52a, the absorption image 52b, and the scattering image 52c can be represented by the following Equations (6) to (8), respectively.

[Formula 4]

$$\phi = \frac{p_2}{2\pi Z_T}(B_s - B_r) \tag{6}$$

$$T = \frac{C_s}{C_r} \tag{7}$$

$$D = \frac{A_s/C_s}{A_r/C_r} \tag{8}$$

where φ is a phase differential image, T is the absorption image, and D is the scattering image (dark-field image). Coefficients with subscripts s and r represent coefficients corresponding to images of the subject 101 captured with and without the subject 101, respectively. $Z_T$ is a distance between the first grating 21 and the second grating 22.

In the fringe scanning method, the phase contrast image 52 is imaged based on values calculated assuming that the second grating is moved in each step by a value that is obtained by dividing the period $p_2$ of the second grating 22 by the number of steps. In other words, values of the coefficients a, b and c in the above Equation (1) are determined by applying the value of the period $p_2$ of the second grating 22 to p that is a value to be set as the period of the intensity change 51. Accordingly, in a case of N=4, because it is assumed that the images acquired in a series of step are images corresponding to phases 1/4, 2/4, 3/4, and 4/4 of the period $p_2$ of the second grating 22, it is necessary to reliably acquire the images corresponding to the phases 1/4 to 4/4 by capturing images while translationally moving the second grating 22. If a shift occurs between the period p of the intensity change 51 acquired and the period $p_2$ of the second grating 22, images (pixel values) corresponding to phases shifted from the phases 1/4 to 4/4 are used for computation, a moire artifact 53 is included as noise components in the phase contrast images 52 generated. That is, in the fringe scanning method, because the phase contrast images 52 are generated by applying each intensity change 51 acquired to the trigonometric function having the same period as the period $p_2$ of the second grating 22, if the phase contrast images 52 are generated by using the fringe scanning method under a condition in which a shift occurs between the period p of the intensity change 51 and the period $p_2$ of the second grating 22, the moire artifact 53 having fringes is formed in each image as shown in FIG. 4.

<Period Shift of Intensity Change>

Figure 5:
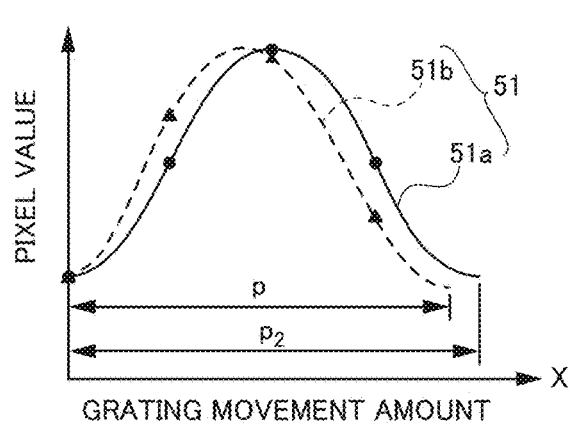
FIG. 5 is a schematic view illustrating a moire artifact appearing in the phase contrast image.

As shown in FIG. 5, a shift occurs between an actual period p of the intensity change 51 and the period $p_2$ of the second grating 22 in some cases. FIG. 5 is a schematic view illustrating an intensity change 51a (solid line in FIG. 5) in a case in which the period p of the intensity change 51 agrees with the period $p_2$ of the second grating 22, and an intensity change 51b (dashed line in FIG. 5) in a case in which a shift occurs between the period p of the intensity change 51 and the period $p_2$ of the second grating 22. Note that although each intensity change 51 actually includes data elements at N points, the data elements at N points are considered as data elements at k-th/N periods in an exemplary view of FIG. 5. If a shift occurs between the total movement amount in a direction perpendicular to the extension direction of the grating pattern of the second grating 22 (scanning direction) and the period $p_2$ of the second grating 22, the period p of the intensity change 51 acquired by the controller 30 is shifted from the period $p_2$ of the second grating 22.

For example, a shift occurs between the set angle that is previously set and an actual angular position of the second grating 22 in some cases. The following equation (9) represents an actual movement amount f of the second grating 22 by the first movement mechanism 41 or the second movement mechanism 42 that is required to move the second grating 22 by a predetermined movement amount (one period $p_2$ of the second grating 22) in the scanning direction of the second grating 22.

[Formula 5]

$$f = \frac{p_2}{\cos\theta} \tag{9}$$

where θ is an angular difference between an actual movement direction of the second grating 22 and the scanning direction. The controller 30 moves the second grating 22 for one period $p_2$ in the scanning direction operating one of the first movement mechanism 41 and the second movement mechanism 42 for moving the grating movement mechanism 40. The controller 30 moves the second grating 22 by the movement amount f calculated using Equation (9) based on the set angle, which is previously set. In this case, if an angular shift occurs between the set angle, which is set, and the actual angular position of the second grating 22, the movement amount f includes a shift caused by a difference between a value of cos θ and a proper value corresponding to the original set angle. Also, even in a case in which such angular shifts are the same amount, the movement amount f becomes larger as a value of θ becomes larger. In other words, if the second grating 22 is moved in the Y or Z direction, which is the movement direction of the second grating 22 moved by the first movement mechanism 41 or the second movement mechanism 42, the shift included in the movement amount f caused by a certain angular shift is small. On the other hand, in a case in which the second grating 22 is moved at an angle of 45 degrees with respect to the Y or Z direction, the shift included in the movement amount f caused by an angular shift from the set angle
becomes large even if this angular shift is the same as
the certain angular shift.

\<Adjustment of Set Value\>

In this embodiment, to reduce the moire artifact 53, the
controller 30 acquires analysis periods Ap (see FIG. 6) each
of which represents the period p of the intensity change 51.
The controller 30 adjusts set values of the movement of the
second grating 22 for generating the phase contrast images
52 based on the analysis periods Ap acquired. Specifically,
the controller 30 adjusts the set values, which are previously
set, prior to generation of the phase contrast images 52 of the
subject 101 captured. In this embodiment, the controller 30
adjusts the set angle as the set value by acquiring an angular
shift of the second grating 22 from the set angle, which is set
as the set value, based on the analysis periods Ap acquired.

Specifically, the controller 30 adjusts the set angle before
capturing images of the subject 101 in installation or regular
maintenance of the phase contrast X-ray imaging system
100. In the adjustment of the set angle, the set angle is
adjusted based on a pixel value of the scattering image 52$c$
in the phase contrast images 52 that is generated by using the
intensity change 51 detected without the subject 101 being
placed. As shown in Equation (8), the pixel value D in the
scattering image 52$c$ is obtained by comparing an image
captured with the subject 101 and an image captured without
the subject 101. In the adjustment of the set angle, two
images that are firstly and secondly captured without the
subject 101 are compared as the image captured with the
subject 101 and the image captured without the subject 101.

In the adjustment of the set angle, the controller 30
acquires the analysis periods Ap (see FIG. 6) by acquiring an
appropriate value of the period p in Equation (1) based on an
amplitude of a pixel value in a background area of the
scattering image 52$c$ generated. Specifically, the controller
30 searches for the appropriate value of the period p based
on the amplitude of the pixel value in the background area
of the scattering image 52$c$ by varying a value of the period
p in Equation (1). The controller 30 acquires a value that
minimizes the amplitude of the pixel value in the back-
ground area of the scattering image 52$c$ as an optimal period.
The background area refers to an area in which the subject
101 is not included in the scattering image 52$c$. In a case in
which an image is captured without the subject 101 being
placed, the entire image corresponds to the background area.
Because the subject 101 is not placed, the pixel value in the
background area is a value that represents a pixel value of
the moire artifact 53. The controller 30 calculates a magni-
tude of an amplitude value of the moire artifact 53 in the
scattering image 52$c$ by varying the value of the period p in
Equation (1), and acquires a value of the analysis period Ap
(see FIG. 6) that represents the proper period p by searching
for the value of the period p that minimizes an amplitude
value. For example, the controller 30 acquires an amplitude
value of the moire artifact 53 by acquiring a standard
deviation of pixel values in the scattering image 52$c$ gen-
erated in the adjustment of the set angle (set value). The
controller 30 acquires a value of the period p that minimizes
the amplitude value of the moire artifact 53 as a value of a
period of the intensity change 51. The analysis period Ap,
which represents the period p of the intensity change 51,
represents a value of the period of the intensity change 51
using a ratio of the period of the intensity change to the
period p$_2$ of the second grating 22.

Figure 6:
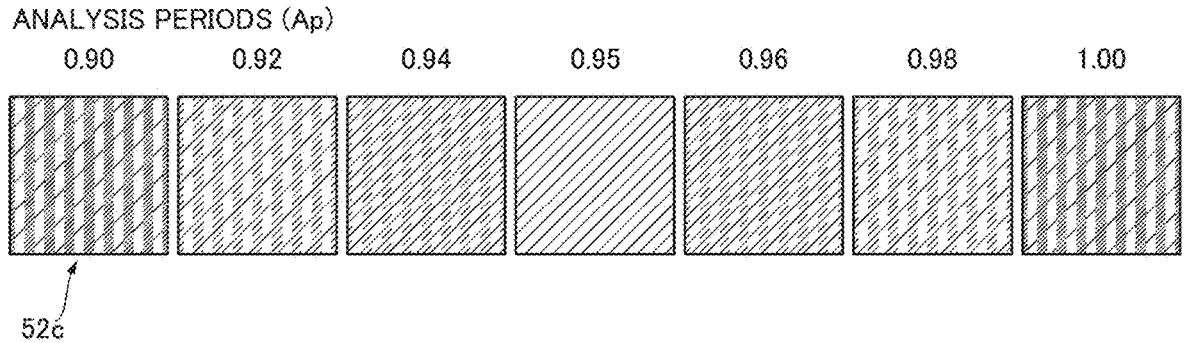
FIG. 6 is a schematic view illustrating changes of the artifact in a case in which the period is varied.

As shown in FIG. 6, as the analysis period Ap is reduced
from 1.00 to 0.95, the moire artifact 53 appearing in each
image is reduced. Also, as the analysis period Ap is further reduced from 0.95, the moire artifact 53 is increased. For
example, in FIG. 6, in a case of the analysis period Ap of
0.95, this means that a period that obtained by multiplying
the period p$_2$ of the second grating 22 by 0.95 (0.95×p$_2$) is
acquired as the period p of the intensity change 51. In other
words, an appropriate value of the analysis period Ap
represents a ratio of a period shift of the period p, which
represents a period of the intensity change 51, to the period
p$_2$ of the second grating 22. In FIG. 6, exemplary scattering
images 52$c$ are illustrated in a case in which the scattering
images are generated by using a plurality of periods that are
reduced with respect to the period p$_2$ of the second grating
22 for the period p of the intensity change 51.

In this embodiment, the controller 30 adjusts the set angle,
which is set, by acquiring the appropriate value of the
analysis period Ap representing the period p of the intensity
change 51. For example, where the set angle of the second
grating 22 is $\theta_2$, a set scanning amount f$_2$ is represented by
the following Equation (10).

[Formula 6]

$$f_2 = \frac{p_2}{\cos\theta_2} \tag{10}$$

Here, the set angle $\theta_2$ represents an inclination of the
scanning direction with respect to a movement direction of
the grating movement mechanism 40. The set scanning
amount f$_2$ is a movement amount (scanning amount) of the
second grating 22 moved by the first movement mechanism
41 or the second movement mechanism 42. In other words,
the set scanning amount f$_2$ is a movement amount by the
grating movement mechanism 40 that is required to move
the second grating 22 by the same distance as the period p$_2$
in the scanning direction. If the set angle $\theta_2$, which is set,
includes an angular shift, the moire artifact 53 will appear in
a case of the set scanning amount f$_2$ that is calculated from
$\theta_2$. In a case in which a current actual grating angle (an
angular position of the second grating 22) is $\theta_0$, an optimal
scanning amount f$_0$, which is an appropriate movement
amount (a required movement amount) of the second grating
22 by the grating movement mechanism 40 for the actual
grating angle $\theta_0$, is represented by the following Equation
(11) by using the calculated appropriate value of the analysis
period Ap. In this case, the current grating angle $\theta_0$ is
calculated by Equation (12).

[Formula 7]

$$f_0 = \frac{f_2}{A_p} \tag{11}$$

$$f_0 = \frac{p_2}{\cos\theta_0} \tag{12}$$

Here, $\Delta\theta$ is introduced to denote an angular shift amount
of the grating angle $\theta_0$, which is the actual angular position
of the second grating 22 with respect to the set angle $\theta_2$,
which is set, and in this denotation the angular shift $\Delta\theta$ is
acquired from the appropriate value of the analysis period
Ap by the following Equation (13).

[Formula 8]

$$\Delta\theta = \theta_0 - \theta_2 \tag{13}$$

$$\Delta\theta = \cos^{-1}\frac{p_2}{f_0} - \theta_2$$

$$\Delta\theta = \cos^{-1}\frac{p_2 * A_p}{f_2} - \theta_2$$

The controller 30 adjusts the set angle by changing a rotation amount of the second grating 22 rotated by the rotation mechanism 43 based on the angular shift amount 40 acquired as discussed above. In other words, the controller 30 adjusts the set angle by changing a control amount for controlling operation of the rotation mechanism 43 in accordance with the set angle $\theta_2$, which is previously set. The controller 30 stores a rotation amount of the rotation mechanism 43 corresponding to the set angle that is adjusted by adjusting the set angle into the storage before capturing an image of the subject 101. That is, the controller 30 updates a rotation amount of the rotation mechanism 43 that has been stored as the set angle by adjusting the set angle.

In a case in which a stepping motor is used as the grating movement mechanism 40, a set scanning amount $f_3$, which is a scanning amount of movement that is set by using a movement resolution r of the stepping motor and a number of pulses s, is represented by the following Equation (14). In this case, an appropriate set angle $\theta_3$ for $f_3$, which is set, is calculated by using Equation (15).

[Formula 9]

$$f_3 = s * r \tag{14}$$

$$f_3 = \frac{p_2}{\cos\theta_3} \tag{15}$$

The resolution r is a dimension of movement per pulse (per one of the pulses s). $f_2$ becomes a nonterminating decimal in some cases, or $f_3 = f_2$ is not satisfied depending on the dimension of resolution r in some other cases. The controller 30 sets a value of $f_3$, which is the movement amount by the grating movement mechanism 40, to make a movement amount of the second grating 22 in the scanning direction agree with a size of one period $p_2$ of the second grating 22, and sets the set angle $\theta_3$ by using Equation (15). Even in such cases, the set angle $\theta_3$ is adjusted by substituting $\theta_3$ and $f_3$ for $\theta_2$ and $f_2$ in Equation (13), respectively.

In this embodiment, in the controller 30, a plurality of set angles are previously set. The controller 30 generates the phase contrast image 52 based on the intensity change 51 of pixel values detected while moving the second grating 22 by a scanning amount that is set at each of the plurality of set angles, which are previously set, by rotating the second grating 22 by using the rotation mechanism 43. For example, the controller 30 stores four set angles of +90 degrees, +45 degrees, 0 degree, and −45 degrees, which are previously set, with the scanning direction that agrees with the Z direction being defined 0 degree. In this embodiment, the controller 30 adjusts each of the plurality of set angles by acquiring the appropriate values of analysis periods Ap at the set angle, which is set. The controller 30 is configured to generate phase contrast images 52 at the plurality of set angles by translating (scanning) the second grating 22 at the adjusted set angles. For example, in a case in which the subject 101 is formed of a fiber-reinforced resin material, fiber orientation of the fibers included in the subject 101 can be visualized by the phase contrast images 52 generated at the plurality of set angles.

(Generation of Phase Contrast Image After Adjustment)

The controller 30 captures images of the subject 101 by capturing the image of the subject 101 with the set angle as the set value being adjusted to generate the phase contrast images 52. The controller 30 acquires the intensity changes 51 that represents the changes in the pixel values of the pixels detected by the detector 12 again by previously adjusting the set angle as the set value as described above while moving the second grating 22 based on the set value (set angle) after adjustment. Here, a period shift is included even in the intensity change 51 after adjustment, which is acquired after the set angle is adjusted, in some cases. For example, an angular shift from the set angle occurs due to an operating accuracy of the rotation mechanism 43, and the angular shift causes a period shift included in the intensity change 51 after adjustment in some cases. To address this, in this embodiment, the controller 30 acquires analysis periods Ap each of which represents the period p of the intensity change 51 detected again. The controller 30 generates the phase contrast images 52 after adjustment by varying the analysis period to eliminate the period shift based on the analysis period Ap acquired again. Note that the angular shift caused by the operating accuracy of the rotation mechanism 43 is smaller than the angular shift adjusted by adjustment of the set angle.

Specifically, the controller 30 acquires the intensity change 51 in the pixel value of each pixel of the detector 12 when an image of the subject 101 is captured similar to adjustment of the set angle before the image of the subject 101 is captured. The controller 30 acquires the appropriate value of the analysis period Ap in the intensity change 51 using the set angle after adjustment based on pixel values in the background area in which the subject 101 is not included similar to adjustment of the set angle. The controller 30 generates phase contrast images 52 after adjustment including the phase differential image 52a, the absorption image 52b and the scatter image 52c by calculating Equation (6) to Equation (8) with the period of the intensity change 51 acquired by the appropriate analysis period Ap being substituted for a value of the period p in Equation (1) and Equation (2). As a result, the controller 30 generates the phase contrast images 52 after adjustment under conditions that the set angle (set value) is adjusted in advance, and that a period shift caused by the operating accuracy of the grating movement mechanism 40 is corrected.

Comparison With Comparative Example

Figure 7:
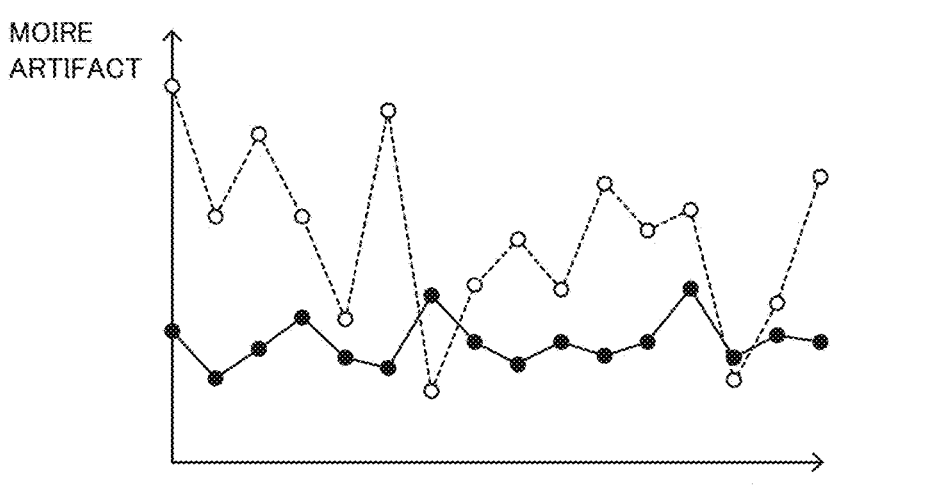
FIG. 7 is a diagram illustrating comparison between conditions with and without adjustment of a set value according to this embodiment.

As shown in FIG. 7, in the phase contrast X-ray imaging system 100 according to this embodiment, the moire artifact 53 in the phase contrast image 52 is reduced by adjusting the set angle (set value) by acquiring the analysis period Ap. In a graph of FIG. 7, an exemplary amount of the moire artifact 53 included in the phase contrast image 52 generated with the set angle being adjusted is shown by a solid line. Also, in a graph of FIG. 7, an exemplary amount of the moire artifact 53 included in the phase contrast image 52 generated without the set angle being adjusted is shown by a dotted line. In the graph of FIG. 7, a vertical axis represents the amount of the moire artifact 53 (e.g., an amplitude of the moire artifact 53). In the graph of FIG. 7, a horizontal axis represents the number of times the phase contrast image 52 is generated. In an exemplary case shown in FIG. 7, the phase contrast image 52 is generated a plurality of times based on the intensity changes 51 detected while translationally moving the second grating 22 in the scanning direction after an angular position of the second grating 22 is moved from 0 degree to 45 degrees, for example. An amount of the moire artifact 53 is larger in the phase contrast image 52 generated without the set angle being adjusted. Contrary to this, although the moire artifact 53 caused by the operating accuracy of the grating movement mechanism 40 is included, the moire artifact 53 is reduced in the phase contrast image 52 generated with the set angle being adjusted as compared with the case in which the set angle is not adjusted.

Image Processing Method

Figure 8:
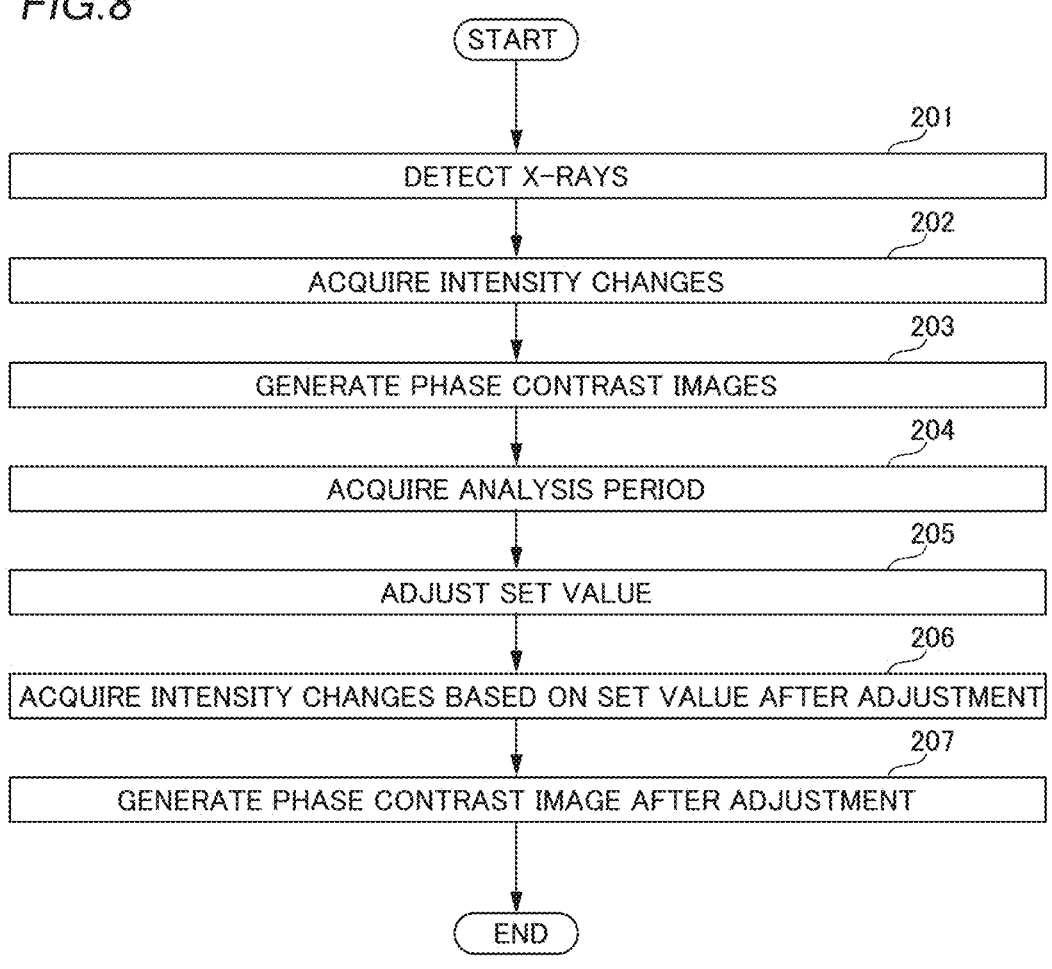
FIG. 8 is a flowchart illustrating an image processing method according to the one embodiment of the present invention.

The following description describes a configuration of an image processing method according to this embodiment with reference to FIG. 8. Control processing in steps 201 to 207 is performed by the controller 30.

In step 201, X-rays for irradiation from the X-ray source 11 that pass through the plurality of gratings 20 (first grating 21, second grating 22, and third grating 23) are detected while the second grating 22 is moved based on a predetermined scanning amount that is previously set.

Subsequently, in step 202, intensity changes 51 that represent changes in pixel values of pixels detected is acquired. Specifically, the intensity changes 51 in the pixel values of the pixels are acquired in data of a plurality of images generated by continuously detecting X-rays while moving the second grating 22.

Subsequently, in step 203, the phase contrast images 52 are generated based on the intensity changes 51 acquired. Specifically, the phase contrast images 52 are generated for values of p by varying a value of the period p in Equations (1) and (2).

Subsequently, in step 204, an analysis period Ap that represents the period p of the intensity change 51 is acquired to reduce the moire artifact 53 as noise components in the phase contrast image 52. Specifically, an appropriate value of the analysis period Ap is acquired based on amplitudes of the moire artifacts 53 in the phase contrast images 52 (scattering images 52c) generated in step 203 by varying the value of the period p in Equations (1) and (2).

Subsequently, in step 205, the set value of the movement of the second grating 22 for generating the phase contrast image 52 is adjusted based on the analysis period Ap acquired. Specifically, the set angle is adjusted as a set value by adjusting a rotation amount of the rotation mechanism 43 corresponding to the set angle that is set.

Subsequently, in step 206, an X-ray image of the subject 101 is captured again while moving the second grating 22 based on the set value (set angle) after adjustment so that intensity changes 51 of pixel values in the pixels in the X-ray image of the subject 101 are acquired.

Subsequently, in step 207, the phase contrast image 52 after adjustment is generated by determining the period p, and coefficients a, b and c of the function represented by Equation (1) by acquiring the appropriate value of the analysis period Ap that represents the period p of the intensity change 51 detected again. After that, the control processing of the image processing method according to this embodiment ends.

Advantages of the Embodiment

In this embodiment, the following advantages are obtained.

In this embodiment, as described above, the phase contrast X-ray imaging system 100 acquires the analysis period Ap that represents a period of the intensity change 51 to reduce the moire artifact 53, which is noise components included in the phase contrast image 52. Subsequently, the phase contrast X-ray imaging system 100 adjusts the set values of movement of the second grating 22 (scanning grating) for generating the phase contrast image 52 based on the acquired analysis period Ap. Accordingly, because the set value of movement of the second grating 22 for generating the phase contrast image is adjusted based on the analysis period Ap acquired, the set value can be adjusted to reduce a shift of actual movement of the grating with respect to the set value of movement of grating. Accordingly, the phase contrast image 52 can be generated based on the intensity changes 51 in the pixel values detected under a condition in which the shift with respect to the set value of movement of grating is reduced. Consequently, it is possible to reduce the moire artifact 53 in the phase contrast image 52 generated even if the shift between the set value of movement of the grating and the actual movement of the grating is large.

In addition, in the phase contrast X-ray imaging system 100 according to this embodiment, following additional advantages can be obtained by configurations discussed below.

That is, in this embodiment, the controller 30 is configured to adjust, as the set value of movement of the second grating 22 (scanning grating) for generating the phase contrast image 52, at least one of a set angle of the second grating 22 in a perpendicular plane perpendicular to an irradiation axis of the X-rays from the X-ray source 11 and a scanning amount of the movement that is set based on the analysis period Ap. According to this configuration, because the set value of the movement of the second grating 22 can be adjusted by adjusting at least one of the set angle of the second grating 22 and the scanning amount that is set, it is possible to reduce a shift of an angular position of the second grating 22 with respect to the set value of the set angle of the second grating 22. Consequently, it is possible to reduce the moire artifact 53 in the phase contrast image 52 generated even if the shift of the actual movement of the second grating 22 with respect to the set value of the set angle of the second grating 22.

In this embodiment, the controller 30 adjusts the set angle by acquiring an angular shift amount 40 of the second grating 22 (scanning grating) with respect to the set angle, which is set, based on the analysis period Ap. Here, in a case in which the actual angular position of the second grating 22 is shifted with respect to the set angle, the moire artifact 53 may occur not only due to the shift of the second grating 22 with respect to the set value but also due to shifts of angular positions between the plurality of gratings 20. In this case, the moire artifact 53 included in the phase contrast image 52 cannot be sufficiently reduced even if the phase contrast image 52 is generated by determining a function waveform from the intensity change 51 of the pixel value. For this reason, because the shifts of the angular positions between the plurality of gratings 20 can be reduced by reducing the angular shift amount Δθ, which represents a magnitude of the actual angular shift of the second grating 22 with respect to the set angle, it is possible to effectively reduce the moire artifact 53 included in the phase contrast image 52.

Also, in this embodiment, the grating movement mechanism 40 includes the rotation mechanism 43 for rotating the second grating 22 (scanning grating) in the perpendicular plane. The controller 30 adjusts the set angle by varying a rotation amount of the second grating 22 rotated by the rotation mechanism 43 based on the angular shift amount Δθ acquired. According to this configuration, in a case in which the angular position of the second grating 22 is changed by rotating the second grating 22 by the rotation mechanism 43, it is possible to effectively reduce the shift of the angular position from the set angle, which is set. Consequently, it is possible to effectively reduce the moire artifact 53 included in the phase contrast image 52 caused by the shift of the angular position in the case in which the second grating 22 is rotated by the rotation mechanism 43.

In this embodiment, the controller 30 acquires, based on the set angle, the intensity changes 51, which represent the changes in the pixel values of the pixels detected by the detector 12, by moving the second grating 22 by using the grating movement mechanism 40 to move the second grating 22 for one period $p_2$ of the second grating 22 in a scanning direction, which is a width direction of the grating pattern of the second grating 22 (scanning grating). The grating movement mechanism 40 moves the second grating 22 for one period $p_2$ of the second grating 22 in the scanning direction of the second grating 22 by moving the second grating 22 by a scanning amount that is set in a predetermined movement direction independently of the angular position of the second grating 22 in the perpendicular plane. Here, if the scanning direction of the second grating 22 is different from the predetermined movement direction (Y or Z direction) in which the second grating 22 is actually moved by the grating movement mechanism 40, the period p of the intensity change 51 in the pixel value of each pixel in the X-ray image with respect to the period $p_2$ of the second grating 22 increases dependently of the angular shift amount, which is a shift amount of the actual angular position of the second grating 22 with respect to the set angle. To address this, the controller 30 is configured to adjust the set angle based on the analysis period Ap acquired when moving the second grating 22 in the predetermined movement direction independently of the angular position of the second grating 22, and as a result it is possible to effectively reduce the moire artifact 53.

In this embodiment, the grating movement mechanism 40 includes a first movement mechanism 41 for moving the second grating 22 in the Y direction (first direction) extending in the perpendicular plane independently of the angular position of the second grating 22 (scanning grating) in the perpendicular plane, and a second movement mechanism 42 for moving the second grating 22 in the Z direction (the second direction) perpendicular to the Y direction in the perpendicular plane. The controller 30 moves the second grating 22 for one period $p_2$ of the second grating 22 in the scanning direction by operating one of the first movement mechanism 41 and the second movement mechanism 42. According to this configuration, a movement amount of the second grating 22 (scanning grating) can be more accurately controlled by moving the second grating 22 by operating only one of the first movement mechanisms 41 and the second movement mechanisms 42 as compared with a case in which operations of both the first movement mechanism 41 and the second movement mechanism 42 are controlled. Accordingly, when the second grating 22 is moved in the Y or Z direction independently of the angular position of the second grating 22, the set angle is adjusted based on the acquired analysis period Ap while the movement amount can be accurately controlled, and as a result it is possible to effectively reduce the moire artifact 53. Consequently, it is possible to further reduce the moire artifact 53 included in the phase contrast image 52.

In this embodiment, the controller 30 generates the phase contrast image 52 including the X-ray scattering image 52c.

The controller 30 acquires the analysis period Ap based on an amplitude of the pixel value in the background area of the scattering image 52c generated. According to this configuration, it is possible to effectively reduce the moire artifact 53 in the scattering image 52c. Consequently, it is possible to effectively improve visibility of the subject 101 in the scattering image 52c.

In this embodiment, the controller 30 acquires, by adjusting the set value of movement of the second grating 22 (scanning grating) for generating the phase contrast image 52, the intensity changes 51 that represent the changes in the pixel values of the pixels detected again by the detector 12 while moving the second grating 22 based on the set value after adjustment. The controller 30 generates the phase contrast image 52 after adjustment by acquiring the analysis period Ap that represents a period of the intensity change 51 detected again. According to this configuration, the moire artifact 53 in the phase contrast image 52 acquired can be reduced by adjusting the set value of movement in advance, and the moire artifact 53 in the phase contrast image 52 after adjustment generated from the intensity change 51 detected again based on the set value after adjustment is further reduced by acquiring the analysis period Ap that represents a period of the intensity change 51 detected again.

In this embodiment, the controller 30 generates the phase contrast image 52 based on the intensity change 51 detected while moving the second grating 22 at the plurality of set angles, which are previously set, by rotating the second grating 22 (scanning grating) by using the rotation mechanism 43. The controller 30 adjusts each of the plurality of set angles by acquiring the analysis period Ap at the set angle. According to this configuration, because the plurality of set angles are adjusted, even in a case in which the phase contrast images 52 are captured at the plurality of set angles, it is possible to effectively reduce the moire artifacts 53 in the plurality of phase contrast images 52.

In this embodiment, the plurality of gratings 20 includes a third grating 23 arranged between the X-ray source 11 and the first grating 21. According to this configuration, coherence of X-rays for irradiation from the X-ray source 11 can be improved by the third grating 23. Accordingly, because a self-image 50 of the first grating 21 can be formed independently of a focal diameter of the X-ray source 11, it is possible to improve a degree of selection freedom of the X-ray source 11.

Modified Embodiments

Note that the embodiment disclosed this time must be considered as illustrative in all points and not restrictive. The scope of the present invention is not shown by the above description of the embodiments but by the scope of claims for patent, and all modifications (modified examples) within the meaning and scope equivalent to the scope of claims for patent are further included.

While the example in which the phase contrast image 52 is generated by moving the second grating 22 (scanning grating) for interfering with the self-image 50 from the first grating 21 in the plurality of gratings 20 in the scanning direction has been shown in the aforementioned embodiment, the present invention is not limited to this. In the present invention, the phase contrast image may be generated by moving the first grating or the third grating in the plurality of gratings. In other words, the first grating or the third grating in the plurality of gratings may serve as the scanning grating. Alternatively, the phase contrast image may be generated by acquiring the intensity change in the pixel value by moving the plurality of gratings. Also, the third grating may be omitted by using an X-ray source for irradiation using high coherent X-rays.

While the example in which the set value of movement of the second grating 22 (scanning grating) is adjusted by adjusting the set angle of the second grating 22 (scanning grating) has been shown in the aforementioned embodiment, the present invention is not limited to this. In the present invention, the set value may be adjusted by adjusting the scanning amount of movement, which is set, of the scanning grating. In an exemplary case, the set scanning amount $f_2$ or $f_3$, which is the scanning amount of movement, which is set, may be adjusted by adjusting the optimal scanning amount $f_0$, which is an optimal movement amount (required movement amount) of the second grating 22 by the grating movement mechanism 40 represented by Equation (11). In this case, if the grating movement mechanism includes a stepping motor, the resolution r in Equation (14) may be reduced by using microstepping, which is a driving technique to make each step angle (resolution r) of the stepping motor even smaller, and the scanning amount as the set value may be adjusted to vary the set scanning amount $f_3$ by varying the number of pulses s to a value corresponding to the optimal scanning volume $f_0$. As an example, in a case in which a number of microsteps of the stepping motor included in the grating movement mechanism is 4, the resolution r is 0.0625 μm/pulse, and when the number of microsteps is changed to 8, the resolution r becomes 0.0125 μm/pulse. A more appropriate set scanning amount $f_3$ can be set in accordance with a value of the optimal scanning amount $f_0$ when the number of microsteps is changed. Note that if the optimal scanning amount $f_0$ becomes a nonterminating decimal, the number of microsteps may be changed to bring the setting scanning amount $f_3$ closer to a value of the optimal scanning amount $f_0$. In an alternative case, in the present invention, both adjustment of the set angle and adjustment of the scanning amount that is set (set scanning amount) may be configured to be adjustable. In this case, one of the set angle and the set scanning amount that is easier to adjust and has a greater effect can be selectively adjusted.

While the example in which the grating movement mechanism 40 moves the second grating 22 in the predetermined movement direction (Y direction or Z direction) independently of the angular position of the second grating 22 (scanning grating) has been shown in the aforementioned embodiment, the present invention is not limited to this. In the present invention, the grating movement mechanism may be configured to vary the direction of movement of the scanning grating dependently of the angular position of the scanning grating.

While the example in which the analysis period Ap representing the period p of the intensity change 51 is acquired based on an amplitude of the pixel value in the background area of the scattering image 52c of the phase contrast image 52 has been shown in the aforementioned embodiment, the present invention is not limited to this. In the present invention, the analysis period may be acquired based not on the scattering image but on the phase differential image or the absorption image. Also, in the fitting of a function representing the intensity change, the analysis period representing the period of intensity change may be acquired based on fitting whose fitting error is small. Also, the intensity change of pixel values detected may be fitted to a periodic function other than the trigonometric function.

While the example in which after the set value is adjusted, the period p of the function representing the intensity change 51 is changed by acquiring the analysis period Ap that represents the intensity change 51 based on the set value after adjustment has been shown in the aforementioned embodiment, the present invention is not limited to this. In the present invention, the phase contrast image may be generated assuming that the period of intensity change of pixel values acquired based on the set value after adjustment is the period of the grating that is previously set. In other words, after the set value of movement is adjusted, the phase contrast image may be generated assuming that the intensity change of the image data acquired by capturing an image of the subject is represented by a function having a period that agrees with the period of the scanning grating.

While the example in which the plurality of set angles are set has been shown in the aforementioned embodiment, the present invention is not limited to this. In the present invention, only one set angle may be previously set.

While the example in which the controller 30 is configured to control operation of the grating movement mechanism 40, operation of the X-ray source 11, generation of the phase contrast image 52, and adjustment of the set value by acquiring the analysis period Ap has been shown in the aforementioned embodiment, the present invention is not limited to this. In the present invention, control devices (hardware) may be configured so that one of the control devices controls some of the operation of the grating movement mechanism, the operation of the X-ray source, the generation of the phase contrast image, and the adjustment of the set value by acquiring the analysis period Ap separately from other device(s).

Modes

The aforementioned exemplary embodiment will be understood as concrete examples of the following modes by those skilled in the art.

Mode Item 1

A phase contrast X-ray imaging system according to mode item 1 includes an X-ray source; a plurality of gratings including a first grating for forming a self-image by irradiation with X-rays from the X-ray source, and a second grating for interfering with the self-image of the first grating; a detector for detecting the X-rays for irradiation from the X-ray source; a grating movement mechanism for moving at least one of the plurality of gratings; and a controller for generating a phase contrast image based on intensity changes that represent changes in pixel values of pixels detected by the detector while moving a scanning grating, which is the at least one of the plurality of gratings, using the grating movement mechanism, wherein the controller is configured to acquire an analysis period that represents a period of the intensity change to reduce a moire artifact as a noise component included in the phase contrast image, and to adjust a set value of movement of the scanning grating for generating the phase contrast image based on the analysis period acquired.

Mode Item 2

In the phase contrast X-ray imaging system according to mode item 1, the controller is configured to adjust, as the set value of movement of the scanning grating for generating the phase contrast image, at least one of a set angle of the scanning grating in a perpendicular plane perpendicular to an irradiation axis of the X-rays from the X-ray source and a scanning amount of the movement that is set based on the analysis period.

Mode Item 3

In the phase contrast X-ray imaging system according to mode item 2, the controller is configured to adjust the set angle by acquiring an angular shift amount of the scanning grating with respect to the set angle, which is set, based on the analysis period.

Mode Item 4

In the phase contrast X-ray imaging system according to mode item 3, the grating movement mechanism includes a rotation mechanism for rotating the scanning grating in the perpendicular plane; and the controller is configured to adjust the set angle by varying a rotation amount of the scanning grating rotated by the rotation mechanism based on the angular shift amount acquired.

Mode Item 5

In the phase contrast X-ray imaging system according to mode item 3 or 4, the controller is configured to acquire, based on the set angle, the intensity changes, which represent the changes in the pixel values of the pixels detected by the detector, by moving the scanning grating by using the grating movement mechanism to move the scanning grating for one period of the scanning grating in a scanning direction, which is a width direction of the grating pattern of the scanning grating; and the grating movement mechanism moves the scanning grating for one period of the scanning grating in the scanning direction by moving the scanning grating by the scanning amount, which is set, in a predetermined movement direction independently of an angular position of the scanning grating in the perpendicular plane.

Mode Item 6

In the phase contrast X-ray imaging system according to mode item 5, the grating movement mechanism includes a first movement mechanism for moving the scanning grating in a first direction extending in the perpendicular plane independently of the angular position of the scanning grating in the perpendicular plane, and a second movement mechanism for moving the scanning grating in a second direction perpendicular to the first direction in the perpendicular plane; and the controller is configured to move the scanning grating for one period of the scanning grating in the scanning direction by operating one of the first movement mechanism and the second movement mechanism.

Mode Item 7

In the phase contrast X-ray imaging system according to any of mode items 1 to 6, the controller is configured to generate the phase contrast image including an X-ray scattering image; and to acquire the analysis period based on an amplitude of a pixel value in a background area of the scattering image generated.

Mode Item 8

In the phase contrast X-ray imaging system according to any of mode items 1 to 7, the controller is configured to acquire, by adjusting the set value of movement of the scanning grating for generating the phase contrast image, the intensity changes that represent changes in the pixel values of the pixels detected again by the detector while moving the scanning grating based on the set value after adjustment, and to generate the phase contrast image after adjustment by acquiring the analysis period that represents a period of the intensity change detected again.

Mode Item 9

In the phase contrast X-ray imaging system according to mode item 4, a plurality of set angles are included as the set angle; and the controller is configured to generate the phase contrast image based on the intensity changes detected while moving the scanning grating at the plurality of set angles, which are previously set, by rotating the scanning grating by using the rotation mechanism, and to adjust each of the plurality of set angles by acquiring the analysis period at the set angle.

Mode Item 10

In the phase contrast X-ray imaging system according to any of mode items 1 to 9, the plurality of gratings include a third grating arranged between the X-ray source and the first grating.

Mode Item 11

An image processing method according to mode item 11 includes detecting X-rays for irradiation from an X-ray source that passes through a plurality of gratings while moving a scanning grating, which is at least one of the plurality of gratings including a first grating for forming a self-image by irradiation with X-rays from the X-ray source and a second grating for interfering with the self-image of the first grating; generating a phase contrast image based on intensity changes that represent changes in pixel values of pixels detected; acquiring an analysis period that represents a period of each intensity change to reduce a moire artifact as a noise component in the phase contrast image generated; and adjusting a set value of movement of the scanning grating for generating the phase contrast image based on the analysis period acquired.

What is claimed is:

1. A phase contrast X-ray imaging system comprising:
an X-ray source;
a plurality of gratings including a first grating for forming a self-image by irradiation with X-rays from the X-ray source, and a second grating for interfering with the self-image of the first grating;
a detector for detecting the X-rays for irradiation from the X-ray source;
a grating movement mechanism for moving at least one of the plurality of gratings; and
a controller for generating a phase contrast image based on intensity changes that represent changes in pixel values of pixels detected by the detector while moving a scanning grating, which is the at least one of the plurality of gratings, using the grating movement mechanism, wherein
the controller is configured
to acquire an analysis period that represents a period of the intensity change to reduce a moire artifact as a noise component included in the phase contrast image, and

23 to adjust a set value of movement of the scanning grating for generating the phase contrast image based on the analysis period acquired.

2. The phase contrast X-ray imaging system according to claim 1, wherein the controller is configured to adjust, as the set value of movement of the scanning grating for generating the phase contrast image, at least one of a set angle of the scanning grating in a perpendicular plane perpendicular to an irradiation axis of the X-rays from the X-ray source and a scanning amount of the movement that is set based on the analysis period.

3. The phase contrast X-ray imaging system according to claim 2, wherein the controller is configured to adjust the set angle by acquiring an angular shift amount of the scanning grating with respect to the set angle, which is set, based on the analysis period.

4. The phase contrast X-ray imaging system according to claim 3, wherein the grating movement mechanism includes a rotation mechanism for rotating the scanning grating in the perpendicular plane; and the controller is configured to adjust the set angle by varying a rotation amount of the scanning grating rotated by the rotation mechanism based on the angular shift amount acquired.

5. The phase contrast X-ray imaging system according to claim 3, wherein the controller is configured to acquire, based on the set angle, the intensity changes, which represent the changes in the pixel values of the pixels detected by the detector, by moving the scanning grating by using the grating movement mechanism to move the scanning grating for one period of the scanning grating in a scanning direction, which is a width direction of the grating pattern of the scanning grating; and the grating movement mechanism moves the scanning grating for one period of the scanning grating in the scanning direction by moving the scanning grating by the scanning amount, which is set, in a predetermined movement direction independently of an angular position of the scanning grating in the perpendicular plane.

6. The phase contrast X-ray imaging system according to claim 5, wherein the grating movement mechanism includes a first movement mechanism for moving the scanning grating in a first direction extending in the perpendicular plane independently of the angular position of the scanning grating in the perpendicular plane, and a second movement mechanism for moving the scanning grating in a second direction perpendicular to the first direction in the perpendicular plane; and the controller is configured to move the scanning grating for one period of the scanning grating in the scanning direction by operating one of the first movement mechanism and the second movement mechanism.

7. The phase contrast X-ray imaging system according to claim 1, wherein the controller is configured to generate the phase contrast image including an X-ray scattering image; and to acquire the analysis period based on an amplitude of a pixel value in a background area of the scattering image generated.

8. The phase contrast X-ray imaging system according to claim 1, wherein the controller is configured to acquire, by adjusting the set value of movement of the scanning grating for generating the phase contrast image, the intensity changes that represent changes in the pixel values of the pixels detected again by the detector while moving the scanning grating based on the set value after adjustment, and to generate the phase contrast image after adjustment by acquiring the analysis period that represents a period of the intensity change detected again.

9. The phase contrast X-ray imaging system according to claim 4, wherein a plurality of set angles are included as the set angle; and the controller is configured to generate the phase contrast image based on the intensity changes detected while moving the scanning grating at the plurality of set angles, which are previously set, by rotating the scanning grating by using the rotation mechanism, and to adjust each of the plurality of set angles by acquiring the analysis period at the set angle.

10. The phase contrast X-ray imaging system according to claim 1, wherein the plurality of gratings include a third grating arranged between the X-ray source and the first grating.

11. An image processing method comprising:

detecting X-rays for irradiation from an X-ray source that passes through a plurality of gratings while moving a scanning grating, which is at least one of the plurality of gratings including a first grating for forming a self-image by irradiation with X-rays from the X-ray source and a second grating for interfering with the self-image of the first grating;

generating a phase contrast image based on intensity changes that represent changes in pixel values of pixels detected;

acquiring an analysis period that represents a period of each intensity change to reduce a moire artifact as a noise component in the phase contrast image generated; and adjusting a set value of movement of the scanning grating for generating the phase contrast image based on the analysis period acquired.

* * * * *